US007108864B1

(12) United States Patent
Martino et al.

(10) Patent No.: US 7,108,864 B1
(45) Date of Patent: *Sep. 19, 2006

(54) TABLET FORMATION

(75) Inventors: Alice C. Martino, Kalamazoo, MI (US); Ashley H. Bates, Sorrento (AU); Walter Morozowich, Kalamazoo, MI (US); E. John Lee, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/656,364

(22) Filed: Sep. 6, 2000

Related U.S. Application Data

(63) Continuation of application No. 09/327,135, filed on Jun. 7, 1999, now Pat. No. 6,177,101.

(60) Provisional application No. 60/088,960, filed on Jun. 11, 1998.

(51) Int. Cl.
*A61K 9/20* (2006.01)

(52) U.S. Cl. .................. 424/464; 424/465; 424/474; 424/489; 424/470; 424/499

(58) Field of Classification Search ............... 424/465, 424/464, 467, 489, 499, 474, 470, 497
See application file for complete search history.

(56) References Cited

U.S. PATENT DOCUMENTS

| | | | |
|---|---|---|---|
| 4,013,785 A * | 3/1977 | Weintraub et al. ............. 424/23 |
| 4,810,775 A | 3/1989 | Bendix et al. | |
| 4,844,907 A * | 7/1989 | Elger et al. ................. 424/465 |
| 5,211,958 A * | 5/1993 | Akkerboom et al. ........ 424/470 |
| 5,225,197 A | 7/1993 | Bolt et al. | |
| 5,256,699 A * | 10/1993 | Murphy et al. ............. 514/658 |
| 5,358,941 A | 10/1994 | Bechard et al. | |
| 5,519,021 A * | 5/1996 | Young et al. ............ 514/230.5 |
| 5,563,142 A | 10/1996 | Palmer et al. | |
| 5,585,115 A | 12/1996 | Sherwood et al. | |
| 5,591,714 A | 1/1997 | Nagarajan et al. | |
| 6,013,280 A | 1/2000 | Frisbee et al. | |
| 6,177,101 B1 * | 1/2001 | Martino et al. ............. 424/464 |
| 6,238,695 B1 * | 5/2001 | Makooi-Morehead ....... 424/451 |

OTHER PUBLICATIONS

Remington: The Science and Practice of Pharmacy 1995 (pp. 1395, 1397, 1398, 1411, 1617-1618).*
Remington: The Science and Practice of Pharmacy, 19$^{th}$ Ed. vol. 1, pp. 194-198 (1995).*
Dictionary of Biochemistry and Molecualar Biology, 2$^{nd}$ ed. 1989, J. Stenesh pp. 269-270.*
Clorpress Package Insert, Bertek Pharmaceutical, Jun. 1998.*
Von. B. Asmussen et al, Drug Release in vitro from Digoxin Formulations with High Bioavailability, Arzneimittelforschung 1980;30(12) :2168-72.

A. F. Davis et al, Effect of supersaturation on membrane transport: 1. Hydrocortisone acetate, Int. J. Pharm. (1991) , 76(1-2) , 1-8.
C. Doherty et al, The In-vitro pH-Dissolution Dependence and In-vivo Bioavailability of Frusemide-PVP Solid Dispersions, J.Pharm.Pharmacol. 41:73-78 (1989).
K.M. O'Driscoll et al, Chlorothiazide-Polyvinylpyrrolidone (PVP) Interactions: Influence on Membrane Permeation (Everted Rat Intestine) and Dissolution, Drug Development and Industrial Pharmacy. 8(4) , 547-564 (1982).
H. Fujioka et al, Biopharmaceutical Studies on Hydantoin Derivatives. III. Physico-chemical Properties, Dissolution Behavior, and Bioavailability of the Molecular Compound of 1-benzenesulfonyl-5,5-diphenylhydantoin and Anti-Pyrine, J. Phar. Dyn. Jul. 1982; 5(7) :475-484.
M. Fujii et al, Dissolution and Bioavailability of Phenobarbital in Solid Dispersion with Phosphatidylcholine, Chem. Pharm. Bull., 39 (7) 1886-1888 (1991).
T. Higuchi, Physical Chemical Analysis of Percutaneous Absorption Process from Creams and Ointments, J.Soc.Cosmet.Chem., 11 (1960) 85-97.
W. I. Higuchi et al, Drug Membrane transport Enhancement Using High Energy Drug-Povidone Coprecipitates, Proc.Int.Symp. on Povodone, pp. 71-79, 1993.
S.L. Raghaven et al, Effect of cellulose polymers on supersaturation and in vitro membrane transport of hydrocortisone acetate, Int. J. Pharm. 193 (2000) 231-237.
N. Kondo et al, Improved Oral Absorption of Enteric Coprecipitates of a Poorly Soluble Drug, J.Pharm.Sci., 83 566-570 (1994).
T. Loftsson et al, The effect of polyvinylpyrrolidone and hydroxypropyl methylcellulose on HPβCD complexation of hydrocortisone and its permeability through hairless mouse skin, Europ.J.Pharm. Sci. 2 (1994) 297-301.
T. Loftsson et al, The effect of water-soluble polymers on aqueous solubility of drugs, Int. J. Pharm. 127 (1996) 293-296.
N.A. Megrab et al, Oestradiol permeation through human skin and silastic membrane: effects of propylene glycol and supersaturation, J.Control.Rel. 36 (1995) 277-294.

(Continued)

*Primary Examiner*—Sreeni Padmanabhan
*Assistant Examiner*—Shahnam Sharareh
(74) *Attorney, Agent, or Firm*—Flynn, Thiel, Boutell & Tanis, P.C.

(57) ABSTRACT

Disclosed is a non-sustained release pharmaceutical tablet composition which comprises a rapidly precipitating drug in an amount from about 5 to about 60% and at least one member selected from the group consisting of a binder in an amount of from about 2 to about 25% and a superdisintegrant in an amount from about 6 to about 40% where the rapidly precipitating drug, "binder" and superdisintegrant are mixed and compressed into a tablet without heating, solvent or grinding.

27 Claims, No Drawings

OTHER PUBLICATIONS

H. Sekikawa et al, Dissolution Behaviors and Gastrointestinal Absorption of Phenytoin in phenytoin-Polyvinylpyrrolidone Coprecipitate, Chem.Pharm.Bull., 26, (1978) 3033-3039.

H. Suzuki et al, Some Factors Influencing the Dissolution of Solid Dispersions with nicotinamide and Hydroxypropylmethylcellulose as Combined Carriers, Chem.Pharm.Bull., 46 1015-1020 (1998).

M.T. Ledwidge et al, Effects of surface active characteristics and solid state forms on the pH solubiity profiles of drug-salt systems, Int.J.Pharm., 174 (1998) 187-200.

Abu T.M. Serajuddin et al, Influence of pH on Release of Phenytoin Sodium from Slow-Release Dosage Forms, J.Pharm.Sci. (1993) 82 (3), 306-310.

H. Suzuki et al, Comparison of Nicotinamide, Ethylurea and Polyethylene Glycol as Carriers for Nifedipine Solid Dispersion Systems, Chem.Pharm.Bull., 45 (1997) 1688-1693.

K. Yamamoto et al, Dissolution Behavior and Bioavailability of Phenytoin from a Ground Mixture with Microcrystalline Cellulose, J.Pharm.Sci. 1976, 65 (10) : 1484-1488.

A.P. Simonelli et al, Inhibition of Sulfathiazole Crystal Growth by Polyvinylpyrrolidone, J.Pharm.Sci., 59 (1970) 633-638.

A.P. Simonelli et al, Dissolution Rates of High Energy Sulfathiazole-Povidone Coprecipitates II: Characterization of Form of Drug Controlling Its Dissolution Rate via Solubility Studies, J.Pharm.Sci., (1976) 65 (3), 355-361.

R. Wald et al, Non-Crystallinity, Supersaturation and Relative Bioavailability: Experiences with a Non-Peptidic HIV-Protease Inhibitor, 10th Annual Meeting of American Assoc. of Pharm. Sci., 1995, (24 pages).

* cited by examiner

TABLET FORMATION

CROSS-REFERENCE TO RELATED APPLICATIONS

This application claims the benefit of U.S. provisional application Ser. No. 60/088,960 filed 11 Jun. 1998, under 35 USC §119(e)(i). This application is a continuation of U.S. application Ser. No. 09/327,135 filed Jun. 7, 1999, now U.S. Pat. No. 6,177,101.

BACKGROUND OF THE INVENTION

1. Field of the Invention

The present invention is a tablet formulation which reduces the rate of precipitation of a rapidly precipitating drug and improves dissolution.

2. Description of the Related Art

U.S. Pat. No. 5,563,142 (EXAMPLE 105) discloses delavirdine.

International Publication WO95/28398 based on PCT patent application PCT/US95/02166 discloses delavirdine mesylate in two crystal forms "S" and "T".

U.S. Pat. No. 5,358,941 discloses a compressed tablet formulation comprising about 0.5 to 40% active ingredient, about 10–80% anhydrous lactose, about 5 to 50% by weight of microcrystalline cellulose, about 0.5 to 10% by weight of croscarmallose sodium and about 0.1 to 5% magnesium stearate. The pharmaceutical tablet formulation of the present invention does not require lactose.

Patent EP 283925 discloses utilization of solvent-based polymers under action of high shearing forces so that precipitation is divided into smallest particles to purify resorbable polyester products. The claimed invention does not co-precipitate polymers in any solvent system with the rapidly precipitating drug prior to formulation with other ingredients, but relies only on close proximity of the dry binder or superdisintegrant with the rapidly precipitating drug in a conventional compressed tablet dosage form.

*International Journal of Pharmaceutics*, 154, 59–66 (1997) discloses the utilization of HPMC, HPC and PVP in a liquid system at various polymer ratios with intent to delay precipitation. Methods discussed include preparation of solid dispersions either by the co-precipitation method of grinding method to improve dissolution properties. The claimed invention utilizes conventional direct compression method of tablet formulation and does not utilize any solid dispersion techniques such as co-precipitation via solvent use or grinding to achieve co-precipitation.

The Handbook of Drug Excipients, 2nd. Ed., edited by A. Wade and P. J. Weller. 1994, page 141, and many other pharmaceutical references, describe the common use of superdisintegrants such as croscarmellose sodium are used to aid tablet disintegration typically in the amount of 1–2% and not more than 5% of the formulation. Higher amounts are not used or recommended due to gelation of the croscarmellose sodium forming a loose matrix which is known to impede dissolution of many drug compounds. The present invention uses greater than 6% croscarmellose sodium.

The Handbook of Drug Excipients, 2nd. Ed., edited by A. Wade and P. J. Weller. 1994, pages 223, 229 and 392, and many other pharmaceutical references, describe the common use of water soluble polymers such as HPMC, HPC-L, and PVP as binders, either as wet binders or dry binders, in immediate and sustained release tablet formulations. For non-sustained release applications, not more than 5% is used of these binders. Higher amounts are not recommended due to impedance of the dissolution rate for many drugs. Amounts higher than 5% of especially HPMC are commonly used only for sustained release dosage forms, and are generally of high molecular weight grades. In the present invention, however, the binder includes use at levels of greater than 5%.

U.S. Pat. No. 5,225,197 discloses a chewable tablet formulation. The present invention is not a chewable tablet.

JP 84-185584 discloses the utilization of HPC, PVP and other binders together with difficulty soluble drugs by use of heat. The claimed invention does not use heat.

SUMMARY OF INVENTION

Disclosed is a non-sustained release pharmaceutical tablet composition which comprises: a rapidly precipitating drug in an amount from about 5 to about 60%, microcrystalline cellulose and at least one member selected from the group consisting of a binder in an amount of from about 2 to about 25% and a superdisintegrant in an amount from about 6 to about 40% where the rapidly precipitating drug, microcrystalline cellulose, binder and superdisintegrant are mixed and compressed into a tablet without heating, solvent or grinding.

Also disclosed is a non-sustained release pharmaceutical tablet composition which is:

| Item | Amount (from about to about) % |
|---|---|
| delavirdine mesylate | 10–40 |
| hydroxypropyl methylcellulose | 5–20 |
| croscarmellose sodium | 6–35 |
| microcrystalline cellulose | 10–50 |
| lactose | 0–15 |
| colloidal silicon dioxide | 0–5 |
| magnesium stearate | 0–5 | where the delavirdine mesylate, microcrystalline cellulose, hydroxypropyl methylcellulose and croscarmellose sodium are mixed and compressed into a tablet without heating, solvent or grinding.

DETAILED DESCRIPTION OF THE INVENTION

The tablets of the present invention require a rapidly precipitating drug (5–60%), microcrystalline cellulose (10–50%), a binder (2–25%) and superdisintegrant (6–40%). While not required, it is often highly desirable to use one or more of the following pharmaceutical ingredients—microcrystalline cellulose (0–50%), lactose (0–80), a flow agent (0–5) and a lubricant (0–5%).

A rapidly precipitating drug is a pharmaceutical compound, or its salt form, which when introduced in water, or simulated physiological fluids at body temperature, begins to dissolve fairly rapidly and then begins to rapidly precipitate out of solution within 60 minutes to a less soluble form which provides a concentration that is less than therapeutic. This precipitation results in slow and incomplete dissolution. In most cases, the amount precipitating can be up to 90% or greater which leaves about 10 or less available for therapeutic activity. It is preferred that the rapidly precipitating drug is a fairly soluble or highly soluble salt form of a poorly soluble free base or free acid drug or an anhydrous form of a poorly soluble free base or free acid drug. The rapidly precipitating drugs are prone to supersaturation as is known to those skilled in the art. It is preferred that the rapidly precipitating drug be selected from the group consisting of delavirdine mesylate, pseudoephedrine, clindamycin hydrochloride, clonidine hydrochloride, diphenhydramine hydrochloride, fluphenazine hydrochloride, hydromorphone hydrochloride, naloxone hydrochloride, oxytetracycline hydrochloride, phenylephrine hydrochloride, pheniramine maleate, tetracycline hydrochloride, verapamil hydrochloride, propoxyphene hydrochloride, hydrocodine bitartrate, acyclovir sodium, albuterol sulfate, ampicillin sodium, benztropine mesylate, benzphetamine hydrochloride, bupivacaine hydrochloride, bupropin hydrochloride, chlorphenamine maleate, chlorpromazine hydrochloride. It is most preferred that the rapidly precipitating drug is delavirdine mesylate. The rapidly precipitating drug should be present in an amount of about 5 to about 60%, preferably in an amount of about 10 to about 40%.

Delavirdine, 1-[5-methanesulfonamidoindolyl-2-carbonyl]-4-[3-(1-methylethyl-amino)-2-pyridinyl]piperazine is known, see U.S. Pat. No. 5,563,142 (EXAMPLE 105). Delavirdine mesylate is also known in two different crystal forms "S" and "T", see, International Publication WO95/28398 based on PCT patent application PCT/US95/02166.

The tablet formulation of the present invention is a non-sustained release pharmaceutical tablet composition which comprises a rapidly precipitating drug in an amount from about 5 to about 60%, microcrystalline cellulose (10–50%) and at least one member selected from the group consisting of a binder in an amount of from about 2 to about 25% and a superdisintegrant in an amount from about 6 to about 40% where the rapidly precipitating drug, microcrystalline cellulose, binder and superdisintegrant are mixed and compressed into a tablet without heating, solvent or grinding. It is preferred that the binder, microcrystalline cellulose and superdisintegrant all be present.

The tablet formulation of the present invention can use a binder. The binder is preferably selected from the group consisting of hydroxypropyl methylcellulose, PVP, hydroxypropyl cellulose, microcrystalline cellulose, hydroxymethylcellulose, carbopol and sodium carboxymethylcellulose; it is more preferred that the binder be selected from the group consisting of hydroxypropyl methylcellulose and more preferably 2910 U.S.P. 3 cps. Also preferred is PVP. It is preferred that the binder be present in an amount of hydroxypropyl methylcellulose of from about 5 to about 20%, PVP from about 2 to about 15%, hydroxypropyl cellulose or hydroxyethylcellulose from about 5 to about 20%, carbopol, methylcellulose, and sodium carboxymethylcellulose from about 3 to about 20%. It is apparent to those skilled in the art that the binders of the present invention are polymeric binders as opposed to non-polymeric binders.

The superdisintegrant is selected from the group consisting of croscarmellose sodium, sodium starch glycolate, L-hydroxypropyl cellulose; it is more preferred that the superdisintegrant be croscarmellose. The superdisintegrant should be present in an amount of from about 6% to about 40%. It is preferred that the superdisintegrant is present in an amount of from about 6 to about 35%; it is more preferred that the superdisintegrant be present in an amount of about 10 to about 30%. This is one of the agents responsible for delaying the precipitation of the rapidly precipitating drug.

The microcrystalline cellulose is not absolutely necessary to prepare the tablet formulation of the present invention. However, it is highly desirable to have it present in most cases. The tablet formulation can use a microcrystalline cellulose diluent.

When present it is preferred that it can be selected from the group consisting of microcrystalline cellulose coarse powder, microcrystalline cellulose medium powder and microcrystalline cellulose 200; it is more preferred that the microcrystalline cellulose be microcrystalline cellulose N.F. coarse powder. The microcrystalline cellulose should be present in an amount of from about 5% to about 50%. It is preferred that the microcrystalline cellulose be present in an amount of from about 10 to about 50%.

The lactose is not absolutely necessary to prepare the tablet formulation of the present invention. However, it is highly desirable to have it present in most cases in an amount up to about 80%. When present it is preferred that it be selected from the group consisting of lactose monohydrate spray process standard, lactose monohydrate, lactose anhydrous, lactose dihydrate, DMV lactose; it is more preferred that the lactose be N.F. monohydrate spray process standard lactose. The lactose can be present in an amount of from about 0% to about 80%. It is preferred that the lactose be present in an amount of from about 5 to about 20%.

The flow agent is not absolutely necessary to prepare the tablet formulation of the present invention. However, it is highly desirable to have it present in most cases. When present it is preferred that it be selected from the group consisting of colloidal silicon dioxide and talc; it is more preferable that the flow agent be selected from the group consisting of colloidal silicon dioxide N.F. When present, the flow agent should be present in an amount up to about 5%. It is preferred that the flow agent be present in an amount of from 0.25 to about 2%.

The lubricant is not absolutely necessary to prepare the tablet formulation of the present invention. However, it is highly desirable to have it present in most cases. When present, it is preferred that the lubricant is selected from the group consisting of magnesium stearate and stearic acid; it is more preferred that the lubricant be magnesium stearate. When present, the lubricant should be present in an amount up to about 5%. It is preferred that the lubricant be present in an amount of 0.25 to about 2%.

As is known to those skilled art, the tablet can be colored, flavored and/or film coated as is known to those skilled in the art.

The tablet composition of the present invention is prepared as is known to those skilled in the art as direct compression. It is preferred to first mix the rapidly precipitating drug with the microcrystalline cellulose very thoroughly by methods well known to those skilled in the art, preferably by use of a high shear mixer. The hydroxypropyl methylcellulose, croscarmellose, lactose, and screened colloidal silicon dioxide are mixed separately, preferably in a high shear mixer, and added to the drug-microcrystalline cellulose mixture and all the ingredients are thoroughly mixed, preferably in a high shear mixer. The magnesium stearate is screened and added to the drug mixture and mixed well. The resulting mixture is compressed by methods well known to those skilled in the art to produce tablets containing the desired amount of active pharmaceutical agent. These tablets can then be film coated and polished as is known to those skilled in the art. These tablets comply with applicable U.S.P. and/or F.D.A. requirements/law and are well suited to commercial production and use. Alternatively, but less preferably, the binder can be solvated and used in a wet granulation process.

Definitions and Conventions

The definitions and explanations below are for the terms as used throughout this entire document including both the specification and the claims.

I. Definitions

Delavirdine refers to 1-[5-methanesulfonamidoindolyl-2-carbonyl]-4-[3-(1-methylethylamino)-2-pyridinyl] piperazine.

Delavirdine mesylate refers to 1-[5-methanesulfonamido-indolyl-2-carbon-yl]-4-[3-(1-methylethylamino)-2-pyridi-nyl]piperazine mesylate salt.

A "rapidly precipitating drug" is a pharmaceutical compound, or its salt form, which when introduced in water, or simulated physiological fluids at body temperature, begins to dissolve fairly rapidly and then begins to rapidly precipitate out of solution within 60 min to a less soluble form which provides a concentration that is less than therapeutic.

All temperatures are in degrees Centigrade.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When two or more solids are used in a mixture, they are expressed as weight/weight designated wt/wt or wt.wt.

PVP refers to polyvinylpyrrolidone.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever.

Those skilled in the art will promptly recognize appropriate variations from the procedures both as to reactants and as to reaction conditions and techniques.

EXAMPLE 1
Delavirdine Mesylate 200 mg Tablet Formulation

| Item | 200 mg tablet Amount/tablet | % (wt.wt) |
|---|---|---|
| delavirdine mesylate | 200.00mg | 30.2 |
| microcrystalline cellulose N.F. coarse powder | 198.76mg | 30.0 |
| lactose NF monohydrate spray process standard | 71.29mg | 10.7 |
| hydroxypropyl methylcellulose 2910 U.S.P. 3 cps | 75.00mg | 11.3 |
| croscarmellose sodium N.F. Type A | 110.00mg | 16.6 |
| colloidal silicon dioxide N.F. | 1.50mg | 0.23 |
| magnesium stearate N.F. powder food grade-V bolted | 5.00mg | 0.76 |

The above tablets are manufactured by intensely mixing the delavirdine mesylate and the microcrystalline cellulose in a high shear mixer. Then add and mix the hydroxypropyl methylcellulose, croscarmellose, lactose, and screened colloidal silicon dioxide in high shear mixer. Finally add screened magnesium stearate and lubricate in high shear mixer. The resulting mixture is compressed, filmcoated, and polished as is known to those skilled in the art to give tablets which have about 200 mg of delavirdine mesylate/tablet and comply with U.S.P. and/or F.D.A. requirements.

The invention claimed is:

1. A non-sustained release non-chewable tablet composition comprising
   (a) a rapidly precipitating drug which is a salt form of a poorly soluble free base that is prone to supersaturation when introduced in water or simulated physiological fluid at body temperature, and more than 90% of it precipitates out within 60 min after coming into contact with said water or simulated physiological fluid at body temperature, with the proviso that the drug is not delavirdine mesylate, is the sole active pharmaceutical ingredient in said composition and is present in an amount from about 5 to about 60%;
   (b) a polymeric binder present in an amount of from 2 to about 25%;
   (c) a superdisintegrant in an amount from about 6 to about 40%; and
   (d) a lubricant present in an amount up to about 5%; and
   wherein the rapidly precipitating drug, polymeric binder, superdisintegrant and lubricant are mixed and compressed into a tablet without heating, solvent or grinding.

2. A non-sustained release, non-chewable tablet composition according to claim 1, wherein the rapidly precipitating drug is selected from clindamycin hydrochloride, clonidine hydrochloride, diphenhydramine hydrochloride, fluphenazine hydrochloride, hydromorphone hydrochloride, naloxone hydrochloride, oxytetracycline hydrochloride, phenylephrine hydrochloride, pheniramine maleate, tetracycline hydrochloride, verapamil hydrochloride, propoxyphene hydrochloride, hydrocodeine bitartrate, acyclovir sodium, albuterol sulfate, ampicillin sodium, benztropine mesylate, benzphetamine hydrochloride, bupivacaine hydrochloride, bupropin hydrochloride, clorphenamine maleate and chlorpromazine hydrochloride.

3. A non-sustained release, non-chewable pharmaceutical tablet composition according to claim 1 where the polymeric binder is selected from the group consisting of:
   hydroxypropyl methylcellulose,
   PVP,
   hydroxypropyl cellulose,
   methylcellulose,
   hydroxyethylcellulose,
   carbopol,
   sodium carboxymethylcellulose.

4. A non-sustained release, non-chewable pharmaceutical tablet composition according to claim 1 wherein the polymeric binder is hydroxypropyl methylcellulose.

5. A non-sustained release, non-chewable pharmaceutical tablet composition according to claim 1 wherein the polymeric binder is PVP.

6. A non-sustained release, non-chewable pharmaceutical tablet composition according to claim 1 where the polymeric binder is present in the amount as follows for:
   hydroxypropyl methyl cellulose of from about 5 to about 20%,
   PVP from about 2 to about 15%,
   hydroxypropyl cellulose from about 5 to about 20%,
   methylcellulose from about 5 to about 20%,
   hydroxyethylcellulose from about 5 to about 20%,
   carbopol from about 3 to about 20%, sodium carboxymethylcellulose from about 3 to about 20%.

7. A non-sustained release, non-chewable pharmaceutical tablet composition according to claim 1 where the superdisintegrant is croscarmellose sodium, sodium starch glycolate or L-hydroxypropyl cellulose.

8. A non-sustained release, non-chewable pharmaceutical tablet composition according to claim 1 where the superdisintegrant is present in an amount of from about 6 to about 35%.

9. A non-sustained release, non-chewable pharmaceutical tablet composition according to claim 8 where the superdisintegrant is present in an amount of from about 10 to about 30%.

10. A non-sustained release, non-chewable pharmaceutical tablet composition according to claim 1 which contains microcrystalline cellulose in an amount up to about 50%.

11. A non-sustained release, non-chewable pharmaceutical tablet composition according to claim 10 where the microcrystalline cellulose is selected from the group consisting of
    microcrystalline cellulose coarse powder
    microcrystalline cellulose medium powder and
    microcrystalline cellulose 200.

12. A non-sustained release, non-chewable pharmaceutical tablet composition according to claim 10 where the microcrystalline cellulose is microcrystalline cellulose N.F. coarse powder.

13. A non-sustained release, non-chewable pharmaceutical tablet composition according to claim 10 where the microcrystalline cellulose is present in an amount of from about 10 to about 40%.

14. A non-sustained release, non-chewable pharmaceutical tablet composition according to claim 1 which contains lactose in an amount up to about 80%.

15. A non-sustained release, non-chewable pharmaceutical tablet composition according to claim 14 where the lactose is selected from the group consisting of lactose monohydrate spray process standard, lactose monohydrate, lactate anhydrous, lactose dihydrate, DMV lactose.

16. A non-sustained release, non-chewable pharmaceutical tablet composition according to claim 14 where the lactose is N.F. monohydrate spray process standard lactose.

17. A non-sustained release, non-chewable pharmaceutical tablet composition according to claim 14 where the lactose is present in an amount of from about 5 to about 20%.

18. A non-sustained release, non-chewable pharmaceutical tablet composition according to claim 1 which contains a flow agent in an amount up to 5%.

19. A non-sustained release, non-chewable pharmaceutical tablet composition according to claim 18 where the flow agent is selected from the group consisting of colloidal silicon dioxide and talc.

20. A non-sustained release, non-chewable pharmaceutical tablet composition according to claim 18 where the flow agent is colloidal silicon dioxide N.F.

21. A non-sustained release, non-chewable pharmaceutical tablet composition according to claim 18 where the flow agent is present in an amount from 0.25 to about 2%.

22. A non-sustained release, non-chewable pharmaceutical tablet composition according to claim 1 where the lubricant is selected from the group consisting of magnesium stearate and stearic acid.

23. A non-sustained release, non-chewable pharmaceutical tablet composition according to claim 22 where the lubricant is magnesium stearate.

24. A non-sustained release, non-chewable pharmaceutical tablet composition according to claim 1 where the lubricant is present in the amount of 0.25 to about 2%.

25. A non-sustained release, non-chewable pharmaceutical tablet composition according to claim 1 where the rapidly precipitating drug is present in an amount of from about 10 to about 40%.

26. A non-sustained release, non-chewable tablet composition according to claim 4, wherein the polymeric binder is hydroxypropyl methylcellulose of from about 5 to about 20%.

27. A non-sustained release, non-chewable tablet composition according to claim 1, wherein the mixing is accomplished in a high shear mixer.

* * * * *